United States Patent [19]

Seufert et al.

[11] 4,428,944
[45] Jan. 31, 1984

[54] TRIFLUOROMETHOXYPHENYL-(DI)THIOPHOSPHORIC ACID ESTERS AND THEIR USE IN PEST CONTROL

[75] Inventors: Walter Seufert, Ludwigshafen; Karl Kiehs, Lampertheim; Gerd Husslein, Bad Durkheim; Juergen Varwig, Heidelberg; Gerhard Hamprecht, Weinheim; Heinrich Adolphi, Limburgerhof, all of Fed. Rep. of Germany

[73] Assignee: BASF Aktiengesellschaft, Fed. Rep. of Germany

[21] Appl. No.: 329,122

[22] Filed: Dec. 9, 1981

[30] Foreign Application Priority Data

Dec. 16, 1980 [DE] Fed. Rep. of Germany ....... 3047242

[51] Int. Cl.³ .......................... A01N 57/14; C07F 9/16
[52] U.S. Cl. ..................................... 424/217; 260/940; 260/950; 260/951; 260/948; 424/210; 424/216
[58] Field of Search .......................... 260/951; 424/217

[56] References Cited

U.S. PATENT DOCUMENTS 3,725,514  4/1973  Tsuchiya et al. ................... 260/951
3,755,511  8/1973  McKendry et al. ................ 260/951
4,139,615  2/1979  Hoffmann et al. .................. 260/949

FOREIGN PATENT DOCUMENTS 814152  9/1951  Fed. Rep. of Germany .

Primary Examiner—Anton H. Sutto
Attorney, Agent, or Firm—Keil & Witherspoon

[57]  ABSTRACT

Trifluoromethoxyphenyl-(di)-thiophosphoric acid esters of the formula

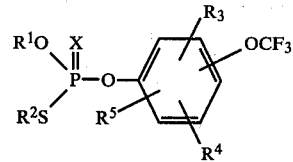

where $R^1$, $R^2$, $R^3$, $R^4$, $R^5$ and X have the meanings given in the description, and their use in pest control.

7 Claims, No Drawings

TRIFLUOROMETHOXYPHENYL-(DI)THIOPHOSPHORIC ACID ESTERS AND THEIR USE IN PEST CONTROL

The present invention relates to trifluoromethoxyphenyl-(di)thiophosphoric acid esters, pesticides containing these compounds as active ingredients, and methods of controlling pests using these active ingredients and agents.

It has been disclosed that O,O-dialkyl O-phenylphosphorothioates have an insecticidal and acaricidal action (German Patent 814,152), and that O,O-dialkyl O(S)-(haloethylphenyl) (di)(thio)phosphates have an insecticidal action (U.S. Pat. No. 3,755,511).

We have found that trifluoromethoxyphenyl-(di)thiophosphoric acid esters of the formula

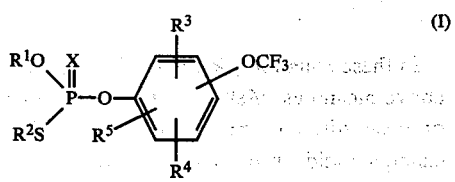

where $R^1$ is alkyl of 1 to 3 carbon atoms, $R^2$ is alkyl or haloalkyl of 1 to 5 carbon atoms, alkoxyalkyl or alkylthioalkyl of 2 to 6 carbon atoms, or cycloalkyl of 3 to 6 carbon atoms, $R^3$, $R^4$ and $R^5$ independently of one another are each hydrogen, halogen, nitro, cyano or alkyl, alkoxy or alkylthio of 1 to 4 carbon atoms and X is oxygen or sulfur, effectively control pests of the insect, arachnid and nematode classes. They have a superior action to that of the known O,O-dialkyl O-phenylphosphorothioates.

In formula I, $R^1$ is alkyl of 1 to 3 carbon atoms, such as methyl, ethyl, n-propyl or i-propyl, $R^2$ is alkyl or haloalkyl of 1 to 5 carbon atoms, such as methyl, ethyl, n-propyl, i-propyl, n-butyl, sec.-butyl, i-butyl, n-pentyl, 1-methyl-n-butyl, 2-chloroethyl or 3-chloro-n-propyl, or is alkoxyalkyl or alkylthioalkyl of 2 to 6 carbon atoms, such as 2-methoxyethyl, 2-ethoxyethyl, 2-isopropoxyethyl, 2-methylthioethyl or 2-ethylthioethyl, or is cycloalkyl of 3 to 6 carbon atoms, such as cyclopentyl or cyclohexyl, and $R^3$, $R^4$ and $R^5$, which may differ, are each hydrogen, halogen, such as chlorine, bromine or fluorine, nitro, cyano or alkyl, alkoxy or alkylthio of 1 to 4 carbon atoms, preferably of 1 to 2 carbon atoms, such as methyl or ethyl.

Preferred compounds of the formula I are those where $R^1$ is ethyl, $R^2$ is alkyl of 3 or 4 carbon atoms, such as n-propyl, i-propyl, sec.-butyl or i-butyl, $R^3$, $R^4$ and $R^5$ independently of one another are each hydrogen or chlorine and X is oxygen or sulfur.

The trifluoromethoxyphenyl-(di)thiophosphoric acid esters of the formula I are obtained by reacting a thiophosphoric acid ester chloride of the formula

where $R^1$, $R^2$ and X have the above meanings, with a trifluoromethoxyphenol of the formula

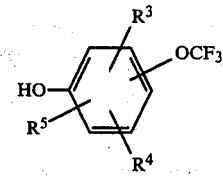

where $R^3$, $R^4$ and $R^5$ have the above meanings, in the presence or absence of an acid acceptor and of a diluent, or with a salt of a trifluoromethoxyphenyl of the formula III in the presence or absence of a diluent.

The course of the reaction can be represented by the following equation:

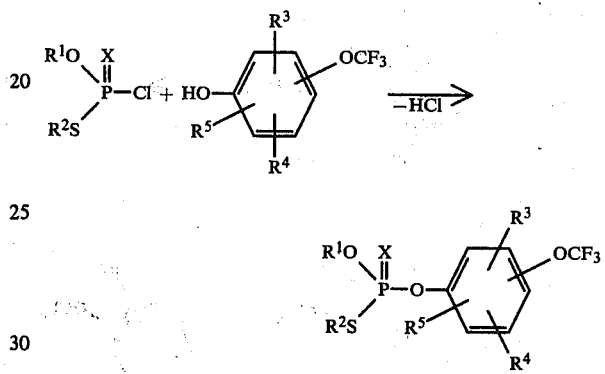

The reaction of a thiophosphoric acid ester chloride of the formula II with a phenol of the formula III can be carried out in an organic diluent, such as acetonitrile, toluene or methyl ethyl ketone, or in a two-phase system, such as toluene/water or methylene chloride/water.

Advantageously, 1 to 2 moles of an acid acceptor per mole of phenol of the formula III are added. An excess of about 10% is preferably used. Suitable acid acceptors are bases, such as alkali metal carbonates, eg. potassium carbonate, alkali metal hydroxides, eg. sodium hydroxide, and tertiary amines, eg. triethylamine. Instead of a base and the phenol, it is equally possible to react a salt of the phenol with the phosphoric acid ester chloride. Suitable salts are the alkali metal salts, alkaline earth metal salts or substituted or unsubstituted ammonium salts, such as alkyl-substituted ammonium salts, for example the sodium, potassium, calcium, ammonium and trimethylammonium salts.

The reaction temperature can be varied within a relatively wide range. In general the reaction is carried out at from 0° to 100° C., preferably at from 20° to 70° C., under atmospheric pressure.

The starting materials are employed in an equimolar ratio. An excess of one or other of the reactants may provide advantages in some cases, but 0.9 to 1.1 moles of phosphoric acid ester chloride are preferably used per mole of phenol.

The reaction mixture is worked up in a conventional manner, for example by adding water and separating the phases. The crude products can be purified by distillation or column chromatography.

O,S-Dialkyl phosphate chlorides are known and can be prepared in a conventional manner (German Laid-Open Application (DOS) 2,642,982; and J. Org. Chem. 30, (1965), 3217). The trifluoromethoxyphenols of the formula III can also be prepared by processes disclosed in the literature (U.S. Pat. Nos. 3,265,741 and 4,157,344; and Zh. Obshch. Khim. 31, (1961), 915–924).

The following processes also lead to compounds of the formula I:

Trifluoromethoxyphenyl-thiophosporic acid esters of the formula Ia can be prepared by subjecting a phosphorous acid ester of the formula IV to an Arbusow reaction with a sulfenyl chloride of the formula $R^2SCl$ in accordance with the following equation:

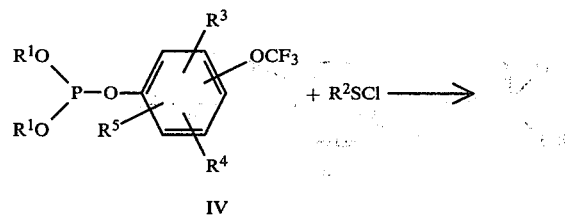

IV

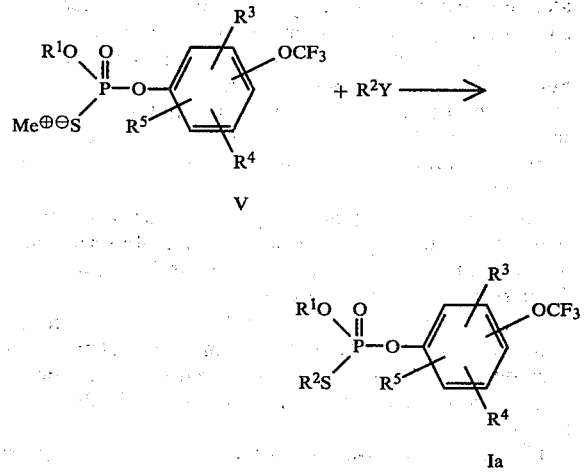

Ia

The trifluoromethoxyphenyl-thiophosphoric acid esters of the formula Ia can also be obtained by alkylating a phosphoric acid ester salt of the formula V with an alkylating agent of the formula $R^2Y$:

V

Ia

Moreover, a phosphoric acid ester dichloride of the formula VI can be reacted with an alcohol or mercaptan of the formula $R^1OH$ or $R^2SH$ to give a compound of the formula I:

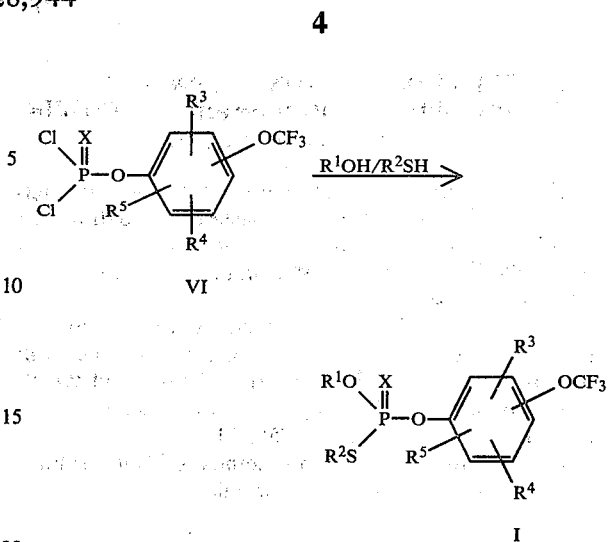

VI

I

In these equations, $R^1$, $R^2$, $R^3$, $R^4$, $R^5$ and X have the above meanings, $Me^\oplus$ is a metal cation or a substituted or unsubstituted ammonium ion and Y is halide, for example iodide, bromide or chloride, or alkylsulfate, for example methylsulfate.

PREPARATION EXAMPLE 0.05 part by weight of diphenyl sulfide is added to a solution of 8.9 parts by weight of 4-trifluoromethoxyphenol in 30 parts by weight of glacial acetic acid, and 6.8 parts by weight of sulfuryl chloride are then added dropwise, without cooling. The mixture is subsequently stirred at room temperature for 3 hours, the solvent is stripped off and the residue is taken up in 50 parts by weight of methylene chloride. This solution is twice washed with 50 parts by weight of saturated bicarbonate solution, and is dried and concentrated. Distillation of the residue under reduced pressure gives 9.8 parts by weight (92% of theory) of 2-chloro-4-trifluoromethoxyphenol of boiling point 70° C./13 mbar.

4.6 parts by weight of potassium carbonate are added to 7.0 parts by weight of 2-chloro-4-trifluoromethoxyphenol in 100 parts by weight of acetonitrile, and the mixture is refluxed for one hour, with stirring. 6.5 parts by weight of O-ethyl S-sec.-butyl phosphorothioate chloride are then added dropwise at 50° C., and the mixture is stirred at 50° C. for 2 hours and then at room temperature for 24 hours. The solvent is removed in a rotary evaporator, 300 parts by weight of toluene and 100 parts by weight of water are added to the residue, the phases are separated, the organic phase is washed with 2 N sodium hydroxide solution and then with water and dried with sodium sulfate and the solvent and volatile impurities are removed at 40° C. under a pressure of 0.1 mbar. 8.7 parts by weight of O-ethyl S-sec.-butyl O-(2-chloro-4-trifluoromethoxyphenyl)-thiophosphate of $n_D^{23} = 1.4795$ are obtained as the residue.

The following compounds of the formula I can be obtained, for example, by a similar method or by one of the other processes described above:

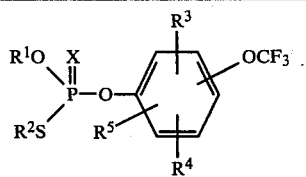

| No. | R¹ | R² | X | Position of OCF₃ | R³ | R⁴ | R⁵ | $n_D$ |
|---|---|---|---|---|---|---|---|---|
| 1 | CH₃ | n-C₃H₇ | S | 2 | H | H | H | |
| 2 | CH₃ | n-C₃H₇ | O | 3 | H | H | H | |
| 3 | CH₃ | n-C₃H₇ | S | 4 | H | H | H | |
| 4 | CH₃ | n-C₃H₇ | O | 2 | H | H | H | |
| 5 | CH₃ | n-C₃H₇ | O | 3 | H | H | H | |
| 6 | CH₃ | n-C₃H₇ | O | 4 | H | H | H | |
| 7 | CH₃ | sec-C₄H₉ | S | 2 | H | H | H | |
| 8 | CH₃ | sec-C₄H₉ | S | 3 | H | H | H | |
| 9 | CH₃ | sec-C₄H₉ | S | 4 | H | H | H | |
| 10 | CH₃ | sec-C₄H₉ | O | 2 | H | H | H | |
| 11 | CH₃ | sec-C₄H₉ | O | 3 | H | H | H | |
| 12 | CH₃ | sec-C₄H₉ | O | 4 | H | H | H | |
| 13 | CH₃ | n-C₃H₇ | O | 2 | H | 4-Cl | H | |
| 14 | CH₃ | n-C₃H₇ | O | 3 | H | 4-Cl | H | |
| 15 | CH₃ | n-C₃H₇ | O | 4 | H | H | 2-Cl | |
| 16 | CH₃ | n-C₃H₇ | O | 2 | H | 4-Br | H | |
| 17 | CH₃ | n-C₃H₇ | O | 3 | H | 4-Br | H | |
| 18 | CH₃ | n-C₃H₇ | O | 4 | H | H | 2-Br | |
| 19 | CH₃ | sec-C₄H₉ | O | 2 | H | 4-Cl | H | |
| 20 | CH₃ | sec-C₄H₉ | O | 3 | H | 4-Cl | H | |
| 21 | CH₃ | sec-C₄H₉ | O | 4 | H | H | 2-Cl | |
| 22 | C₂H₅ | n-C₃H₇ | O | 2 | H | H | H | |
| 23 | C₂H₅ | n-C₃H₇ | O | 3 | H | H | H | |
| 24 | C₂H₅ | n-C₃H₇ | O | 4 | H | H | H | |
| 25 | C₂H₅ | n-C₃H₇ | O | 2 | H | 4-Cl | H | |
| 26 | C₂H₅ | n-C₃H₇ | O | 3 | H | H | H | |
| 27 | C₂H₅ | n-C₃H₇ | O | 4 | H | H | H | |
| 28 | C₂H₅ | n-C₃H₇ | O | 2 | H | H | H | |
| 29 | C₂H₅ | n-C₃H₇ | O | 3 | H | H | H | $n_D^{27} = 1.4670$ |
| 30 | C₂H₅ | n-C₃H₇ | O | 4 | H | H | H | |
| 31 | C₂H₅ | n-C₃H₇ | O | 2 | H | 4-Cl | H | |
| 32 | C₂H₅ | n-C₃H₇ | O | 3 | H | 4-Cl | H | |
| 33 | C₂H₅ | n-C₃H₇ | O | 4 | H | H | 2-Cl | $n_D^{25} = 1.4795$ |
| 34 | C₂H₅ | n-C₃H₇ | O | 2 | H | 4-Br | H | |
| 35 | C₂H₅ | n-C₃H₇ | O | 3 | H | 4-Br | H | |
| 36 | C₂H₅ | n-C₃H₇ | O | 4 | H | H | 2-Br | |
| 37 | C₂H₅ | n-C₃H₇ | O | 2 | 6-Cl | 4-Cl | H | |
| 38 | C₂H₅ | n-C₃H₇ | O | 3 | 6-Cl | 4-Cl | H | |
| 39 | C₂H₅ | n-C₃H₇ | O | 4 | 6-Cl | 4-Cl | H | |
| 40 | C₂H₅ | n-C₃H₇ | O | 2 | 6-Br | 4-Br | H | |
| 41 | C₂H₅ | n-C₃H₇ | O | 3 | 6-Br | 4-Br | H | |
| 42 | C₂H₅ | n-C₃H₇ | O | 4 | 6-Br | H | 2-Br | |
| 43 | C₂H₅ | n-C₃H₇ | O | 2 | H | 5-CH₃ | H | |
| 44 | C₂H₅ | n-C₃H₇ | O | 3 | H | 5-CH₃ | H | |
| 45 | C₂H₅ | n-C₃H₇ | O | 4 | H | 5-CH₃ | H | |
| 46 | C₂H₅ | n-C₃H₇ | O | 2 | H | 4-CN | H | |
| 47 | C₂H₅ | n-C₃H₇ | O | 3 | H | 4-CN | H | |
| 48 | C₂H₅ | n-C₃H₇ | O | 4 | 3-CN | H | H | |
| 49 | C₂H₅ | n-C₃H₇ | S | 2 | H | H | H | |
| 50 | C₂H₅ | n-C₃H₇ | S | 3 | H | H | H | $n_D^{26} = 1.4975$ |
| 51 | C₂H₅ | n-C₃H₇ | O | 4 | H | H | H | |
| 52 | C₂H₅ | n-C₃H₇ | S | 2 | H | 4-Cl | H | |
| 53 | C₂H₅ | n-C₃H₇ | S | 3 | H | 4-Cl | H | |
| 54 | C₂H₅ | n-C₃H₇ | S | 4 | 2-Cl | H | H | $n_D^{24} = 1.5100$ |
| 55 | C₂H₅ | n-C₃H₇ | S | 2 | H | 4-Br | H | |
| 56 | C₂H₅ | n-C₃H₇ | S | 3 | H | 4-Br | H | |
| 57 | C₂H₅ | n-C₃H₇ | S | 4 | 2-Br | H | H | |
| 58 | C₂H₅ | i-C₃H₇ | O | 2 | H | H | H | |
| 59 | C₂H₅ | i-C₃H₇ | O | 3 | H | H | H | |
| 60 | C₂H₅ | i-C₃H₇ | O | 4 | H | H | H | |
| 61 | C₂H₅ | i-C₃H₇ | O | 2 | H | 4-Cl | H | |
| 62 | C₂H₅ | i-C₃H₇ | O | 3 | H | 4-Cl | H | |
| 63 | C₂H₅ | i-C₃H₇ | O | 4 | 2-Cl | H | H | |
| 64 | C₂H₅ | i-C₃H₇ | O | 2 | H | 4-Br | H | |
| 65 | C₂H₅ | i-C₃H₇ | O | 3 | H | 4-Br | H | |
| 66 | C₂H₅ | i-C₃H₇ | O | 4 | H | H | 2-Cl | |
| 67 | C₂H₅ | sec-C₄H₉ | O | 2 | H | H | H | |
| 68 | C₂H₅ | sec-C₄H₉ | O | 3 | H | H | H | $n_D^{26} = 1.4683$ |
| 69 | C₂H₅ | sec-C₄H₉ | O | 4 | H | H | H | |
| 70 | C₂H₅ | sec-C₄H₉ | O | 2 | H | 4-Cl | H | |
| 71 | C₂H₅ | i-C₃H₇ | O | 3 | H | 4-Cl | H | |

-continued

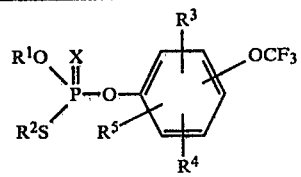

| No. | R¹ | R² | X | Position of OCF₃ | R³ | R⁴ | R⁵ | $n_D$ |
|---|---|---|---|---|---|---|---|---|
| 72 | C₂H₅ | i-C₃H₇ | O | 4 | Cl | H | H | $n_D^{23} = 1.4795$ |
| 73 | C₂H₅ | i-C₃H₇ | O | 2 | H | 4-Br | H | |
| 74 | C₂H₅ | i-C₃H₇ | O | 3 | H | 4-Br | H | |
| 75 | C₂H₅ | i-C₃H₇ | O | 4 | 2-Br | H | H | |
| 76 | C₂H₅ | i-C₃H₇ | O | 2 | H | 4-Cl | 6-Cl | |
| 77 | C₂H₅ | i-C₃H₇ | O | 3 | H | 4-Cl | 6-Cl | |
| 78 | C₂H₅ | i-C₃H₇ | O | 4 | 2-Cl | H | 6-Cl | |
| 79 | C₂H₅ | i-C₃H₇ | O | 2 | H | 4-Br | 6-Br | |
| 80 | C₂H₅ | i-C₃H₇ | O | 3 | H | 4-Br | 6-Br | |
| 81 | C₂H₅ | i-C₃H₇ | O | 4 | 2-Br | H | 6-Br | |
| 82 | C₂H₅ | i-C₃H₇ | O | 2 | H | H | 4-CN | |
| 83 | C₂H₅ | i-C₃H₇ | O | 3 | 2-CN | H | H | |
| 84 | C₂H₅ | i-C₃H₇ | O | 4 | H | 4-CN | H | |
| 85 | C₂H₅ | i-C₃H₇ | O | 2 | H | H | 5-CH₃ | |
| 86 | C₂H₅ | sec-C₄H₉ | O | 3 | H | H | 5-CH₃ | |
| 87 | C₂H₅ | sec-C₄H₉ | O | 4 | H | H | 5-CH₃ | |
| 88 | C₂H₅ | sec-C₄H₉ | O | 2 | H | 4-F | H | |
| 89 | C₂H₅ | sec-C₄H₉ | O | 3 | H | 4-F | H | |
| 90 | C₂H₅ | sec-C₄H₉ | O | 4 | 2-F | H | H | |
| 91 | C₂H₅ | sec-C₄H₉ | S | 2 | H | H | H | |
| 92 | C₂H₅ | sec-C₄H₉ | S | 3 | H | H | H | |
| 93 | C₂H₅ | sec-C₄H₉ | S | 4 | H | H | H | |
| 94 | C₂H₅ | sec-C₄H₉ | S | 2 | H | 4-Cl | H | |
| 95 | C₂H₅ | sec-C₄H₉ | S | 3 | H | 4-Cl | H | |
| 96 | C₂H₅ | sec-C₄H₉ | S | 4 | 2-Cl | H | H | |
| 97 | C₂H₅ | i-C₄H₉ | S | 2 | H | H | H | |
| 98 | C₂H₅ | i-C₄H₉ | O | 3 | H | H | H | |
| 99 | C₂H₅ | i-C₄H₉ | O | 4 | H | H | H | |
| 100 | C₂H₅ | i-C₄H₉ | O | 2 | H | 4-Cl | H | |
| 101 | C₂H₅ | i-C₄H₉ | O | 3 | H | 4-Cl | H | |
| 102 | C₂H₅ | i-C₄H₉ | O | 4 | 2-Cl | H | H | $n_D^{23} = 1.4780$ |
| 103 | C₂H₅ | i-C₄H₉ | O | 2 | H | 4-Br | H | |
| 104 | C₂H₅ | i-C₄H₉ | O | 3 | | 4-Br | H | |
| 105 | C₂H₅ | i-C₄H₉ | O | 4 | 2-Br | H | H | |
| 106 | C₂H₅ | i-C₄H₉ | S | 2 | H | H | H | |
| 107 | C₂H₅ | i-C₄H₉ | S | 3 | H | H | H | |
| 108 | C₂H₅ | i-C₄H₉ | S | 4 | H | H | H | |
| 109 | C₂H₅ | i-C₄H₉ | S | 2 | H | 4-Cl | H | |
| 110 | C₂H₅ | i-C₄H₉ | S | 3 | H | 4-Cl | H | |
| 111 | C₂H₅ | i-C₄H₉ | S | 4 | 2-Cl | H | H | |
| 112 | C₂H₅ | CH₃O—(CH₂)₂— | O | 2 | H | H | H | |
| 113 | C₂H₅ | CH₃O—(CH₂)₂— | O | 3 | H | H | H | |
| 114 | C₂H₅ | CH₃O—(CH₂)₂— | O | 4 | H | H | H | |
| 115 | C₂H₅ | CH₃O—(CH₂)₂— | O | 2 | H | 4-Cl | H | |
| 116 | C₂H₅ | CH₃O—(CH₂)₂— | O | 3 | H | 4-Cl | H | |
| 117 | C₂H₅ | CH₃O—(CH₂)₂— | O | 4 | 2-Cl | 4 | H | |
| 118 | C₂H₅ | CH₃O—(CH₂)₂— | O | 2 | H | 4-Br | H | |
| 119 | C₂H₅ | CH₃O—(CH₂)₂— | O | 3 | H | 4-Br | H | |
| 120 | C₂H₅ | CH₃O—(CH₂)₂— | O | 4 | 2-Br | H | H | |
| 121 | C₂H₅ | C₂H₅O—(CH₂)₂— | O | 2 | H | H | H | |
| 122 | C₂H₅ | C₂H₅O—(CH₂)₂— | O | 3 | H | H | H | |
| 123 | C₂H₅ | C₂H₅O—(CH₂)₂— | O | 4 | H | H | H | |
| 124 | C₂H₅ | C₂H₅O—(CH₂)₂— | O | 2 | H | 4-Cl | H | |
| 125 | C₂H₅ | C₂H₅O—(CH₂)₂— | O | 3 | H | 4-Cl | H | |
| 126 | C₂H₅ | C₂H₅O—(CH₂)₂— | O | 4 | H | H | 2-Cl | |
| 127 | C₂H₅ | C₂H₅O—(CH₂)₂— | O | 2 | H | 4-Br | H | |
| 128 | C₂H₅ | C₂H₅O—(CH₂)₂— | O | 3 | H | 4-Br | H | |
| 129 | C₂H₅ | C₂H₅O—(CH₂)₂— | O | 4 | 2-Br | H | H | |
| 130 | C₂H₅ | i-C₃H₇O—(CH₂)₂— | O | 2 | H | H | H | |
| 131 | C₂H₅ | i-C₃H₇O—(CH₂)₂— | O | 3 | H | H | H | |
| 132 | C₂H₅ | i-C₃H₇O—(CH₂)₂— | O | 4 | H | H | H | |
| 133 | C₂H₅ | i-C₃H₇O—(CH₂)₂— | O | 2 | H | 4-Cl | H | |
| 134 | C₂H₅ | i-C₃H₇O—(CH₂)₂— | O | 3 | H | 4-Cl | H | |
| 135 | C₂H₅ | i-C₃H₇O—(CH₂)₂— | O | 4 | 2-Cl | H | H | |
| 136 | C₂H₅ | i-C₃H₇O—(CH₂)₂— | O | 2 | H | 4-Br | H | |
| 137 | C₂H₅ | i-C₃H₇O—(CH₂)₂— | O | 3 | H | 4-Br | H | |
| 138 | C₂H₅ | i-C₃H₇O—(CH₂)₂— | O | 4 | 2-Br | H | H | |
| 139 | C₂H₅ | CH₃—(CH₂)₂—CH(CH₃)— | O | 2 | H | H | H | |
| 140 | C₂H₅ | CH₃—(CH₂)₂—CH(CH₃)— | O | 3 | H | H | H | |
| 141 | C₂H₅ | CH₃—(CH₂)₂—CH(CH₃)— | O | 4 | H | H | H | |
| 142 | C₂H₅ | C₅H₉ | O | 2 | H | H | H | |

-continued

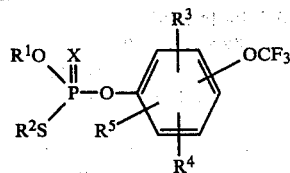

| No. | R¹ | R² | X | Position of OCF₃ | R³ | R⁴ | R⁵ | $n_D$ |
|-----|-----|-----|---|---|-----|-----|-----|-----|
| 143 | C₂H₅ | C₅H₉ | O | 3 | H | H | H | |
| 144 | C₂H₅ | C₅H₉ | O | 4 | H | H | H | |
| 145 | C₂H₅ | ClCH₂—(CH₂)₂— | O | 2 | H | H | H | |
| 146 | C₂H₅ | ClCH₂—(CH₂)₂— | O | 3 | H | H | H | |
| 147 | C₂H₅ | ClCH₂—(CH₂)₂— | O | 4 | H | H | H | |

The trifluoromethoxyphenyl-(di)thiophosphoric acid esters of the formula I according to the invention are suitable for effectively combating pests from the classes of insects, arachnids and nematodes. They may be employed as pesticides for protecting crops, and in the hygiene, stores protection and veterinary sectors.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimalus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ocis, Chrysomya macellaria, Chrysomya hominivorax, Lucilia cuprina, Lucilia sercata,* and *Hypoderma lineata;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

Examples from the Nemathelminthes class are rootknot nematodes, e.g.; *Meloidogyne incognita, Meloidogyne hapla,* and *Meloidogyne javanica,* cyst-forming nematodes, e.g., *Globodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus*

*multicinctus, Radopholus similis, Belonolaimus longicaudatus, Longidorus elongatus,* and *Trichodorus primitivus.*

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

Examples of formulations are given below.

I. 5 parts by weight of compound no. 18 is intimately mixed with 95 parts by weight of particulate kaolin. A dust is obtained containing 5% by weight of the active ingredient.

II. 30 parts by weight of compound no. 29 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 33 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

IV. 20 parts by weight of compound no. 53 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

V. 80 parts by weight of compound no. 50 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

The active ingredients may also be successfully used in the ultra-low volume method, where it is possible to apply formulations containing more than 95 wt% of active ingredient, or even the 100% active ingredient.

When the active ingredient are applied in the open, the rates are from 0.2 to 10, preferably 0.5 to 2.0, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

Examples of active ingredients which may be admixed are as follows:

1,2-dibromo-3-chloropropane, 1,3-dichloropropene, 1,3-dichloropropene+1,2-dichloropropane, 1,2-dibromomethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methyl-carbamoyl)-oxy]-1-thiooxamidate, N-(2-methyl-4-chlorophenyl)-N,N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-diimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethylO-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzyl-furyl-(3)-methyl-DL-cis,trans-chrysanthemate, 3-phenoxybenzyl(±)-cis,trans-2,2-dimethyl-3-(2,2-dichlorovinyl)-cyclopropanecarboxylate, α-cyano-3-phenoxybenzyl(±)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furyl-methylchrysanthemate, and α-cyano-3-phenoxybenzyl-α-isopropyl-4-chlorophenylacetate.

The following examples illustrate the biological action of the new compounds.

The active ingredients are numbered as in the foregoing table.

EXAMPLE 1

Continuous contact action on houseflies (*Musca domestica*)

Both covers and bottoms of Petri dishes 10 cm in diameter are lined with a total (per dish) of 2 ml of acetonic solutions of the active ingredients. After the solvent has evaporated (about 30 mins.), 20 4-day old flies are introduced into the dishes. The kill rate is determined after 4 hours.

In this test, a very high kill rate is achieved with compounds nos. 29, 33, 50, 54 and 68.

EXAMPLE 2

Contact action and the effect of ingested food on caterpillars of the diamondback moth (*Plutella maculipennis*)

Leaves of young cabbage plants are dipped for 3 seconds in aqueous emulsions of the active ingredients and, after excess liquid has been briefly allowed to drip off, placed on a moist filter paper in a Petri dish. 10 caterpillars of the 4th stage are then placed on each leaf. The action is assessed after 48 hours.

In this test, the following compounds, for example, had a very good action: 29, 33, 50, 54, 68 and 102.

EXAMPLE 3

Contact action on oriental cockroaches (*Blatta orientalis*)

The bottoms of 1 liter preserving jars is lined with acetonic solutions of the active ingredients. After the solvent has evaporated, 5 adult cockroaches are introduced into each jar. The kill rate is determined after 48 hours.

In this test, compounds nos. 29, 33, 50, 54, 68, 72 and 102 have an excellent action.

EXAMPLE 4

Contact action on granary weevils (*Sitophilus granarius*)

Petris dishes 10 cm in diameter are lined with acetonic solutions of the active ingredients. After the solvent has evaporated, 100 granary weevils are placed in each dish.

After 4 hours, the weevils are transferred to untreated vessels. The kill rate is determined after 24 hours, by counting how many weevils are, after this period has elapsed, capable of leaving an untreated cardboard dish (40 mm in diameter, 10 mm high) within 60 minutes.

In this test, compounds nos. 29, 33, 50, 54, 68 and 72 have a very good action.

EXAMPLE 5

Contact action on ticks (*Ornithodorus moubata*)

Ticks in the 3rd larval stage are placed in paper bags and dipped for 3 seconds in the emulsion under investigation. The bags are then suspended. The action on the ticks is assessed after 48 hours.

In this test, compounds nos. 29, 33 and 68 have a very good action.

EXAMPLE 6

Systemic action on caterpillars (*Prodenia litura*)

200 ml of quartz sand is introduced into 250 ml plastic beakers in 8-vessel trays. 5 grains of Indian corn are placed in each beaker, about 1 cm below the surface. 50 ml of water is then added to each beaker, and transparent plastic covers are then fitted over the trays. The covers are removed after 8 days, and treatment is carried out after 10 days by pouring 40 ml of aqueous active ingredient formulations on to the plants; one day later, 50 ml of dry quartz sand is added so as to prevent the animals coming into contact with the treated surface.

A plastic cylinder (7 cm in diameter) is then placed on each beaker, 5 caterpillars in the 3rd larval stage are introduced, and the cylinders are covered with a wire gauze.

The damage caused, and the kill rate are assessed after 4 days.

In this test, compounds nos. 29, 30, 50, 54, 68, 72 and 102 have a good action.

EXAMPLE 7

Breeding experiment with houseflies larvae (*Musca domestica*)

50 g of a culture medium consisting of 10 parts of baker's yeast, 10 parts of dried milk, 100 parts of water and 1 part of agar is thoroughly mixed, while warm, with the aqueous active ingredient formulations. After the medium has cooled, approx. 0.1 ml of flies' eggs is placed on it and their development is observed for a week. The temperature is kept at 20° C.

In this test, compounds nos. 29, 33, 50, 54, 68, 72 and 102 have a good action.

EXAMPLE 8

Action on nematodes (*Ditylenchus dipsaci*)

Nematodes (Ditylenchus dipsaci) freshly extracted from living plant tissue are suspended in pure tapwater. Aqueous active ingredient formulations are added to such suspensions, and the kill rate is assessed after 4 and 24 hours.

In this test, compounds nos. 29, 33, 50, 54, 68, 72 and 102 have a good action.

We claim:

1. A trifluoromethoxyphenyl-(di)thiophosphoric acid ester of the formula

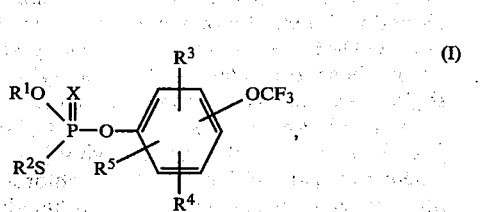

where $R^1$ is alkyl of 1 to 3 carbon atoms, $R^2$ is alkyl of 1 to 5 carbon atoms or alkoxyalkyl of 2 to 6 carbon atoms, $R^3$, $R^4$ and $R^5$ independently of one another are each hydrogen or halogen, and X is oxygen or sulfur.

2. A trifluoromethoxyphenyl-(di)thiophosphoric acid ester of the formula I as defined in claim 1, wherein $R^1$ is ethyl, $R^2$ is alkyl of 3 or 4 carbon atoms, $R^3$, $R^4$ and $R^5$ independently of one another are hydrogen or chlorine and X is oxygen or sulfur.

3. O-Ethyl-S-n-propyl-O-(4-trifluoromethoxyphenyl)-thiophosphate.

4. O-Ethyl-S-n-propyl-O-(2-trifluoromethoxyphenyl)-thiophosphate.

5. O-Ethyl-S-n-propyl-O-(3-trifluoromethoxyphenyl)-thiophosphate.

6. A pesticide containing inert additives and a trifluoromethoxyphenyl-(di)thiophosphoric acid ester of the formula I as defined in claim 1.

7. A process for combating pests, wherein an effective amount of a trifluoromethoxyphenyl-(di)thiophosphoric acid ester of the formula I as defined in claim 1 is allowed to act on the pests and/or their habitat.

* * * * *